United States Patent [19]

Higa et al.

[11] Patent Number: 4,801,606

[45] Date of Patent: Jan. 31, 1989

[54] ANTIVIRAL COMPOSITIONS

[75] Inventors: Tatsuo Higa, Okinawa; Shinichi Sakemi, Vero Beach, both of Japan; Sue S. Cross, Ft. Pierce, Fla.

[73] Assignee: Harbor Branch Oceanographic Institution Inc., Ft. Pierce, Fla.

[21] Appl. No.: 74,977

[22] Filed: Jul. 17, 1987

[51] Int. Cl.⁴ .................... A61K 31/35; C07D 493/04
[52] U.S. Cl. ..................................... 514/452; 549/364
[58] Field of Search ......................... 549/364; 514/452

Primary Examiner—John M. Ford
Attorney, Agent, or Firm—Carroll F. Palmer

[57] ABSTRACT

This invention relates to novel compositions which are useful as antitumor, antiviral and antifungal compositions, a process of producing the compositions and a method for inhibiting tumors, viruses and fungi utilizing the composition. More particularly, the novel compositions are derived from marine sponge Theonella sp.

5 Claims, No Drawings

ANTIVIRAL COMPOSITIONS

FIELD OF THE INVENTION

This invention relates to a new organic compositions which have useful antitumor, antiviral and antifungal activity. Additionally and particularly, this invention relates to new antitumor, antiviral and antifungal compositions derived from a marine organism, i.e., the sponge Theonella sp. and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well know, e.g., cancer is second only to heart and vascular diseases as a cause of death in man.

Viral diseases inflict man, plants, insects, and animals. The prevention and control of viral diseases have important health and economic implications.

Viral diseases contribute to inflictions in humans including common colds, herpes and cancer and the importance of their control is obvious. Also important is control of viral diseases in animals for economic reasons as well as the ability of such animals to become virus reservoirs or carriers which facilitate the spreading of viral diseases to humans. Viral plant diseases have been known to have a disruptive effect on the cultivation of fruit trees, tobacco, and various vegetables. Insect viral diseases are also of interest because of the insects' ability to transfer viral diseases to humans.

Prevention of the growth of fungus and the infections and maladies caused by it to mammals and plants is also of importance to man. The presence of fungus may cause various diseases and infections in man including mycotic disease, e.g., pulmonary candidiasis and pulmonary blastomycosis. Certain yeastlike organisms, e.g., Cryptococcus neoformans, may cause serious infections of the central nervous system. More commonly known fungal infections in humans and mammals include ringworm, which are fungus infections of hair and nail areas, as well as resistant infections of the skin. Many other fungal infections inflict humans and mammals in the areas of skin, mucous membranes, intestinal tract, vaginal area and lungs.

Plants are also attacked by various fungi. Damage caused by fungus infection to agriculture amounts to billions of dollars annually. Various inorganic and organic fungistats and fungicides have been tried but with limited success. It is of course important for the fungistat or fungicide to kill the fungi but not the plant and to leave no toxic residue on the food of the plant. Various methods have been utilized to combat fungus infection in agriculture including foliage fungicide by which method plants are coated with a preventive weather-resistant fungicide. Seed treatment and soil treatment are methods which require fungicides which are safe for seeds and resist degradation by soil and soil microorganisms. Chemotherapeutants are fungicides which permeate the plant to protect new growth or eliminate infections which have already occurred within the plant. Agricultural fungistats and fungicides and their application must also meet very stringent requirements and regulations, which have been promulgated, for example, in the United States.

Considerable research and resources have been devoted to oncology and antitumor measures including chemotherapy; antiviral measures; and combating fungal infections in both mammals and plants. While various antitumor, antiviral or antifungal agents and methods have been developed which aid in inhibiting tumors, viruses and the spread of fungus, respectively, additional methods and chemical agents are needed.

A potential source for antitumor, antiviral, and antifungal compositions is marine plant and animal life and of particular interest are marine sponges. It has now been found that organic compositions derived from extracts of the sponge Theonella sp. possess useful antitumor, antiviral and antifungal activity.

Some compounds of interest have been previously isolated from marine sponge Theonella, sp. In particular sesquiterpenoid compounds have been reported by H. Nakamura, J. Kobayashi, Y. Ohizumi, and Y. Hirata *Tetrahedron Letters*, Vol. 5, No. 47, pp. 5401–5404 (1984). This paper discloses the isolation from the Okinawan sea sponge Theonella cf. swinhuei of "theonellin" compositions of the formulae:

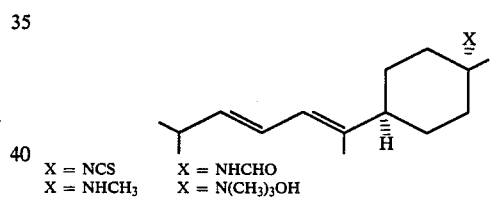

X = NCS   X = NHCHO
X = NHCH₃   X = N(CH₃)₃OH

No biological activity was reported by Nakamura et al. for theonellin compositions. Also of interest are misakinolide compositions, having antitumor and antiviral properties, described in co-pending patent application Ser. No. 051,127 filed on May 18, 1987 by T. Higa, R. Sakai and M. Lui.

Another naturally derived composition of interest is pederin. Pederin is isolated from insects of the Paederus genus. Pederin has the following structure:

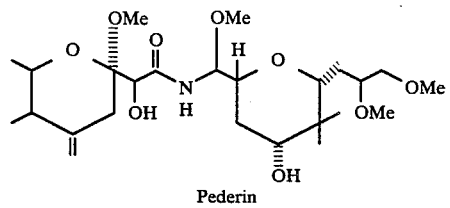

Pederin

Pederin shows antimitotic activity as described in British patent specification Nos. 1,078,049 (1967) and 932,875 (1963).

SUMMARY OF THE INVENTION

It is therefore an object of the invention to provide novel compositions which are useful as antitumor, antiviral and antifungal agents and a process for producing such novel compositions.

It is an additional object of the invention to provide a method for inhibiting tumors, viruses and fungus growth and resultant infection and disease utilizing novel antitumor, antiviral and antifungal compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the formulae:

wherein $X^1$-$X^4$ are the same or different and are a hydrogen, hydroxyl, lower acyl, or lower alkyl group; $x^5$-$x^6$ are the same or different and are a hydrogen or lower alkyl group; Y is either no substituent or a lower alkyl group; $R^1$ is a hydrogen, hydroxyl, lower alkyl, or lower alkoxy group; $R^2$-$R^5$ are the same or different and are a hydrogen, hydroxyl, lower alkoxy or lower acyloxy group; $Q^1$-$Q^3$ are the same or different and are a hydrogen, nitro, amino, lower acylamino, or lower alkyl group; and $Z^1$ is a hydrogen, alkyl, hydroxyl, alkoxy, amino, mono- or dialkly amino, or α-amino acid residue. In other embodiments of the invention the double ponds in the formulae I-III are partially or fully reduced.

In preferred embodiments of the invention, the compositions are substantially pure.

In further preferred embodiments the compositions have the structure IV-VI:

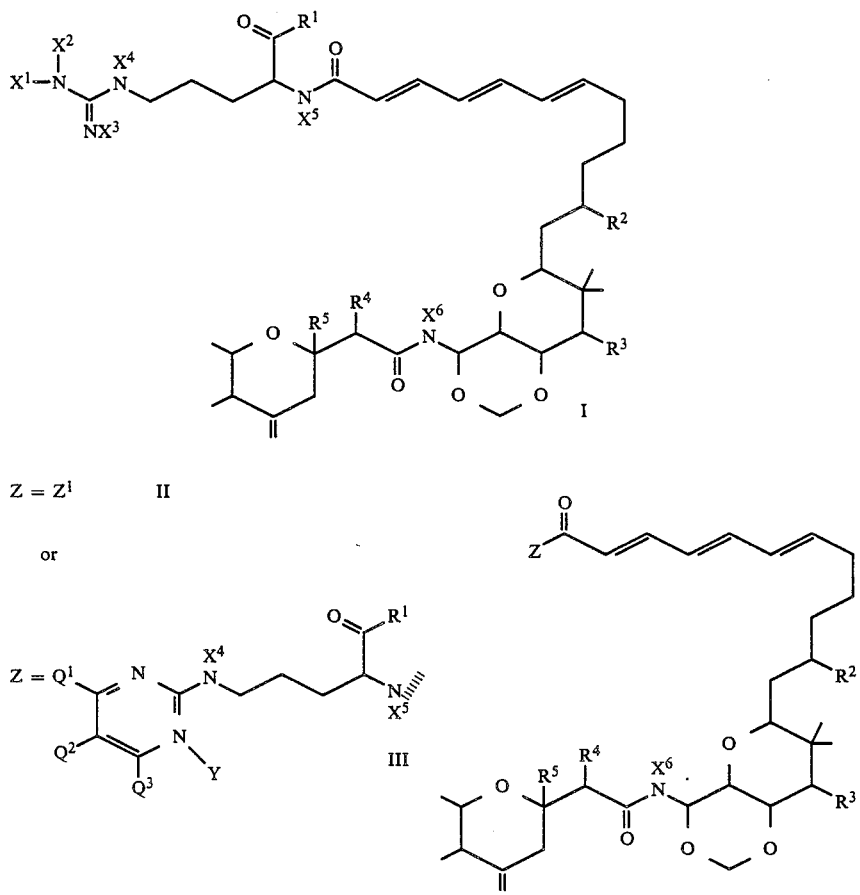

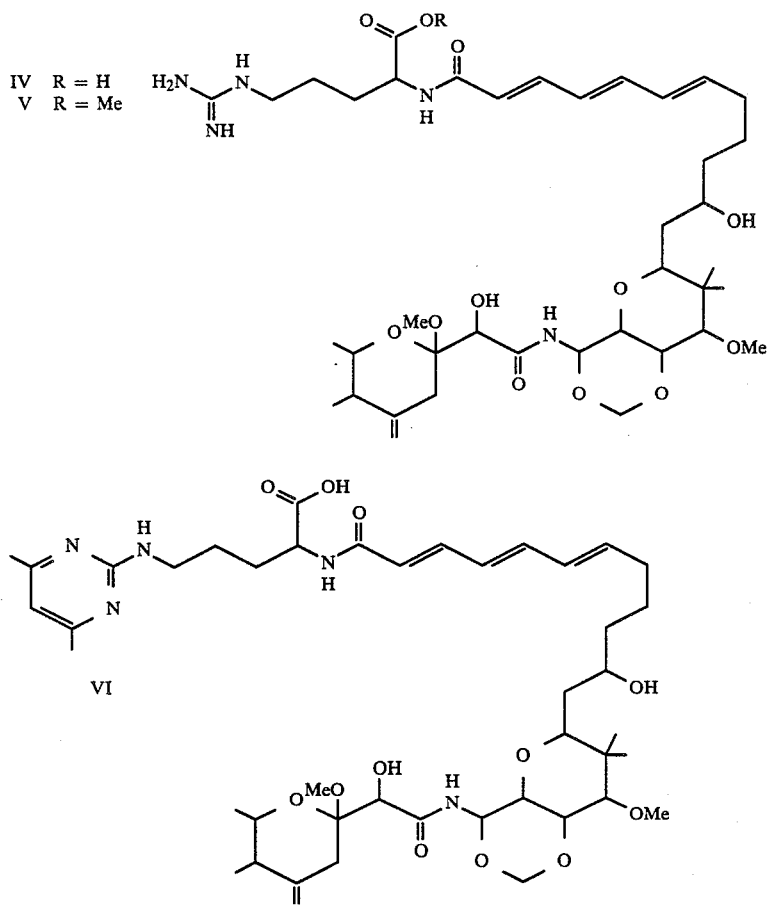

As embodied and fully described herein, the invention also comprises an antitumor, antiviral or antifungal composition comprising, as active ingredient, an effective antitumor, antiviral or antifungal amount, respectively, of the composition of the invention and a nontoxic pharmaceutically acceptable carrier or diluent.

As embodied and fully described herein, the invention also comprises a process to produce the compositions of the invention. The process comprises the steps of collecting marine sponge Theonella, sp. contacting the marine sponge with a suitable organic solvent system to obtain an extract; fractionating the extract; and isolating the compositions of the invention from the fractionated extract.

As embodied and fully described herein, the invention further comprises a method for inhibiting tumors comprising contacting tumor cells with an effective antitumor amount of a composition of the invention.

As embodied and fully described herein, the invention further comprises method for inhibiting viruses comprising contacting viruses with an effective antiviral amount of a composition of the invention.

As embodied and fully described herein, the invention further comprises a method for inhibiting the growth of or killing fungi comprising contacting fungi with an effective antifungal amount of a composition of the invention.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following examples section.

In accordance with the invention novel compositions are provided to achieve the objects in accordance with the purposes of the invention, as embodied and fully described herein, the invention comprises compositions of the general formulae I–III:

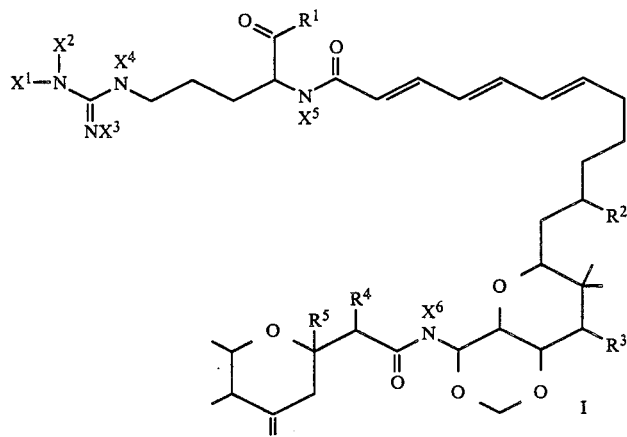

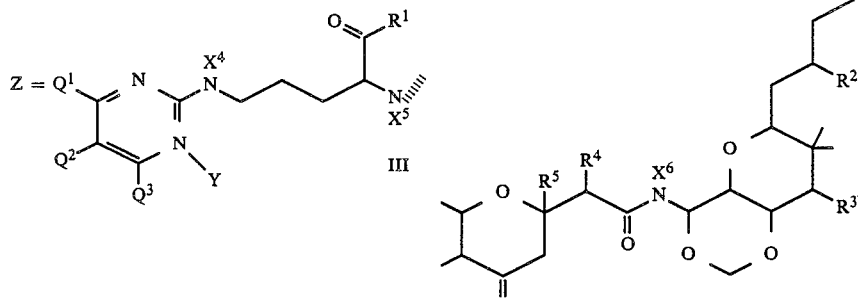

wherein $X^1$-$X^4$ are the same or different and are a hydrogen, hydroxyl, lower acyl, or lower alkyl group; $X^5$-$X^6$ are the same or different and are a hydrogen or lower alkyl group; Y is either no substituent or a lower alkyl group; $R^1$ is a hydrogen, hydroxyl, lower alkyl, or lower alkoxy group; $R^2$-$R^5$ are the same or different and are a hydrogen, hydroxyl, lower alkoxy or lower acyloxy group; $Q^1$-$Q^3$ are the same or different and are a hydrogen, nitro, amino, lower acylamino, or lower alkyl group; and $Z^1$ is a hydrogen, alkyl, hydroxyl, alkoxy, amino, mono- or dialkly amino, or α-amino acid residue. In other embodiments of the invention the double bonds in the formulae I–III are partially or fully reduced.

In preferred embodiments of the invention, the compositions are substantially pure.

In further preferred embodiments the compositions of the invention have the formulae IV–VI:

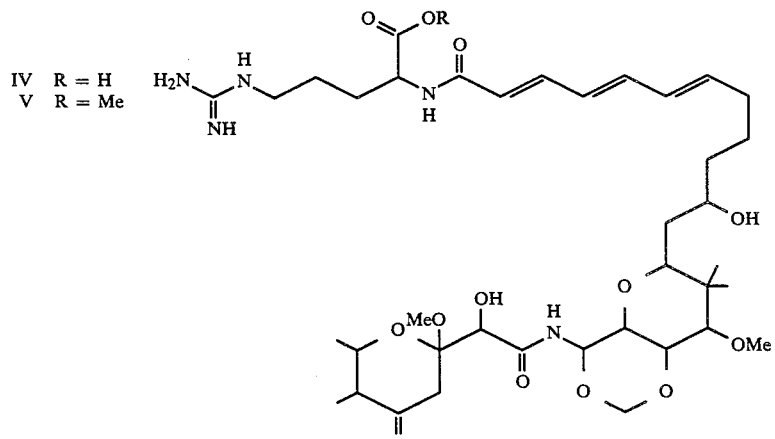

IV  R = H
V   R = Me

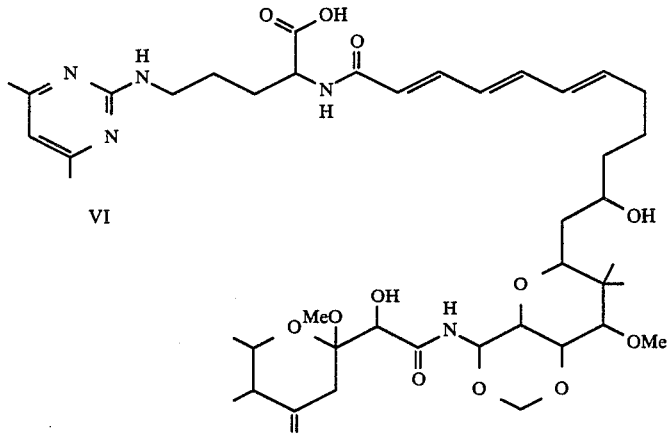

VI

In accordance with the invention, antitumor compositions are provided comprising as active ingredient an effective antitumor amount of one or more compositions of the invention and a non-toxic pharmaceutically acceptable carrier or diluent. While effective amounts may vary, as conditions in which an antitumor compositions are used vary, a minimal dosage required for activity is generally between 0.001 and 10 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of the compositions of the invention. The compositions of the invention are active for inhibiting a diverse range of tumors including, but not limited to P388 mouse leukemia cells, human lung, colon and mammary tumors such as lung carcinoma A-549, ileocecal adenocarcinoma HCT-8, and human breast adenocarcinoma cells MDA-MB-231. The effectiveness of the compositions of the invention for inhibiting tumors cells and tumors indicates their usefulness for controlling tumors in hosts including mammals and for treating cancerous cachexia.

In accordance with the invention, antiviral compositions are provided comprising as active ingredient an effective antiviral amount of the compositions of the invention and a non-toxic pharmaceutically acceptable carrier or diluent. While effective amounts may vary, as conditions in which antiviral compositions are used vary, a minimal dosage required for activity is generally between 0.0002 to 20 micrograms against 25 to 80 plaque forming units of virus. The compositions of the invention are active for inhibiting or killing a diverse range of viruses including, but not limited to, RNA viruses, vesicular stomatitis (herein "VSV") adeno-, corona-, reo- and influenza viruses and the DNA virus, herpes simplex-I and II (herein "HSV-I" and "HSV-II") adeno- and papova- viruses. Useful examples of non-toxic pharmaceutically acceptable carriers or diluents include, but are not limited to, the following: ethanol, dimethyl sulfoxide and glycerol.

In accordance with the invention, a method for inhibiting viruses in a host is provided comprising contacting viruses with an antiviral amount of the compositions of the invention. The effectiveness of the compositions of the invention for inhibiting viruses indicates their usefulness for controlling viruses and virus related diseases in hosts including mammals and plants.

In accordance with the invention, antifungal compositions are provided comprising as active ingredient effective antifungal amounts of the compositions of the invention and a non-toxic pharmaceutically acceptable carrier or diluent. While effective amounts may vary, as conditions in which an antifungal compositions are used vary, a minimal dosage required for activity is generally between 5 and 50 micrograms/ml against $10^3$ml fungi, such as *Candida albicans* for example. Useful examples of non-toxic pharmaceutically acceptable carriers or diluents include, but are no limited to, the following: ethanol, dimethyl sulfoxide and glycerol.

In accordance with the invention, a method for inhibiting fungus in a host is provided comprising contacting fungus with an antifungal amount of the compositions of the invention. The effectiveness of the compositions of the invention for inhibiting fungus indicates their usefulness for controlling fungus and fungus related diseases in hosts including mammals. Further, these compositions may be useful as agricultural fungicides.

In accordance with the invention, a process is provided to produce the compositions of the invention. The process comprises the steps of collecting samples of the marine sponge Theonella, sp. contacting the marine sponge with a suitable organic solvent system to obtain an extract; partitioning said extract by chromatography to obtain a number of fractions; and isolating the compositions of the invention from the fractionated extract.

In preferred embodiments of the invention the suitable organic solvent system is selected from the group of solvents consisting of ethyl acetate, methanol, heptane, hexanes, isooctane, acetone, benzene, toluene, diethyl ether, t-butyl-methyl ether, methylene chloride, chloroform, ethanol, isopropanol, 1,2-dichloroethane, dichloromethane, and mixtures thereof. Particularly preferred extracting solvents are ethyl acetate and methanol.

While those solvents listed above are the presently preferred choices for the solvents useful in accordance with the invention, other suitable solvents may be substituted. A suitable solvent system should be capable of extracting the compositions of the invention from other components of the sponge. Different ratios of solvents and any combination may be used in the solvent system of the invention as would be known to those skilled in the art.

Compositions according to the invention are isolated by various fractionation, and chromatographic techniques and/or synthesized from the extracts obtained. Any suitable fractionation and isolation techniques as known to those skilled in the art may be utilized in accordance with the process of the invention. Preferred isolation techniques include various chromatography techniques such as column chromatography with suitable stationary phases as would be known to those skilled in the art (e.g., polystyrene NS gel) eluted with a suitable solvent such as, for example, heptane, methanol, dichloromethane, ethyl acetate, hexanes, isooctane, chloroform, dichloromethane, 1,2-dichloroethane, benezene, toluene, isopropanol, n-butanol, water, ethanol, diethyl ether and mixtures thereof. Particularly preferred eluents are chloroform, methanol, water and mixtures thereof.

A more detailed description and explanation of a preferred embodiment of the process of the invention to produce the compositions of the invention is provided in the examples section.

It is therefore apparent that the compositions of the invention, the process for producing the compositions of the invention and the methods for utilizing the compositions of the invention to inhibit tumors, viruses and fungus growth fulfill the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing the compositions of the invention.

The following examples represent preferred embodiments of the compositions, processes and methods of the invention for satisfying the stated objects of the invention. The starting materials and reagents in the example whose methods of preparation are not indicated are commercially available from sources known to the art such as chemical supply houses.

EXAMPLES 1-3

Preparation of

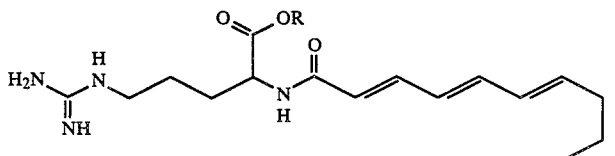

1 R = H
2 R = Me

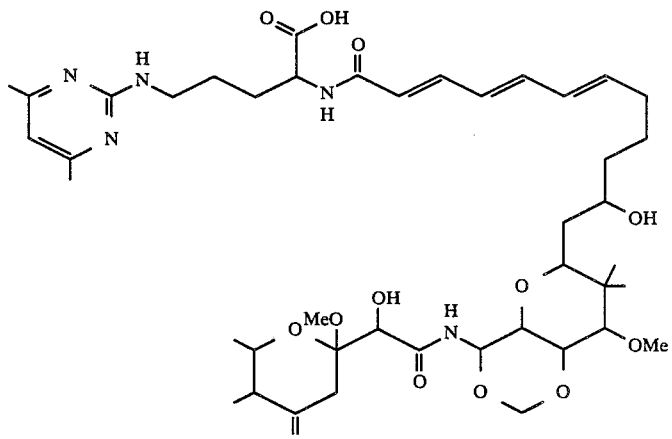

3

A 7.5 kg (wet weight) sample of a sponge, Theonella sp. collected off Onna, Okinawa in 50 feet of water was extracted by soaking in methanol (8 liters) for two days. After decanting the extract, the material was soaked in fresh methanol (8 liters) and extracted in the same manner. The combined extract was concentrated to about 300 ml of aqueous suspension and then extracted with ethyl acetate (300 ml×3). The aqueous phase was concentrated to dryness and extracted with methanol (500 ml) to give 114 gms. of brown solid. A part (100 gms.) of this solid was leaded on a column of polystyrene gel (NS gel) and eluted first with water and then with methanol. The methanol eluate (19.77 gms.) was separated on silica gel by eluting initially with 3:1 chloroform-methanol and then with increasing proportional amounts of methanol. The fractions eluted with 2:1 to 1:1 chloroform-methanol were combined (total 4.32 gms.) and partitioned between the upper and lower layers of 13:7:8 chloroform-methanol-water. The lower layer (1.79 gms.) was repeatedly separated by countercurrent chromatography using 2:3:10:6 of 1,2-dichloroethane-chloroform-methanol-water (mobile phase, upper layer) to furnish 470 mg of onnamide (1) as a light yellow glass, $[\alpha]_D^{20}+99.1°$ (c 5.5, methanol).

Onnamide A(1) exhibited the following spectral data: High resolution FABMS m/z 794.4557 [calcd for $C_{39}H_{64}N_5O_{12}$ (M+H) 794.4551]; UV (methanol) $\lambda_{max}202$ ($\epsilon$7500) and 299 nm (38800); IR (KBr) 3360 br, 2965, 2935, 1650 br, 1950 br, 1512 br, 1450 br, 1391, 1320 br, 1305 sh, 1265, 1226, 1194, 1170, 1130 sh, 1092, 1071, 1030, 1008, 910, 880, and 788 cm$^{-1}$; $^1$H NMR (CD$_3$OD) $\delta$7.13 (1H, dd, J=15.0, 11.2 Hz), 6.50 (1H, dd, J=14.8, 10.7 Hz), 6.23 (1H, dd, J=14.7, 11.3 Hz), 6.19 (1H, dd, J=14.7, 10.8 Hz), 6.07 (1H, d, J=15.1 Hz), 5.93 (1H, dt, J=15.2, 6.9 Hz), 5.79 (1H, d, J=9.2 Hz), 5.48 (1H, d, J=6.9 Hz), 4.80 (1H, d, J=6.9 Hz), 4.79 (1H, br s), 4.63 (1H, br s), 4.36 (1H, dd, J=7.9, 5.3 Hz), 4.23 (1H, s), 4.16 (1H, dd, J=9.7, 6.5 Hz), 3.98 (1H, dd, J=9.0, 6.6 Hz), 3.87 (1H, dd, J=2.4, 6.5 Hz), 3.64 (1H, m), 3.62 (1H, d, J=9.6 Hz), 3.55 (3H, s), 3.47 (1H, dd, J=8.1, 3.6 Hz), 3.22 (3H, s), 3.19 (2H, m), 2.40 (1H, br d, J=14.3 Hz), 2.32 (1H, br d, J=14.4 Hz), 2.25–2.05 (3H, m), 1.89 (1H, m), 1.75 (1H, m), 1.63 (2H, m), 1.62–1.37 (5H, m), 1.28 (1H, m), 1.17 (3H, d, J=6.5 Hz), 1.00 (3H, s), 0.96 (3H, d, J=6.9 Hz), and 0.85 (3H, s); $^{13}$C NMR (CD$_3$OD) $\delta$179.01 (s), 174.27 (s), 168.28 (s), 158.67 (s), 148.14 (s), 141.93 (d), 141.15 (d), 140.42 (d), 131.46 (d), 129.48 (d), 124.37 (d), 110.12 (t), 101.27 (s), 87.58 (t), 80.59 (d), 78.74 (d), 75.48 (d), 74.88 (d), 73.99 (d), 71.03 (d), 70.78 (d×2), 61.93 (q), 55.62 (d), 48.78 (q), 42.96 (d), 42.17 (s), 42.04 (t), 37.27 (t), 36.84 (t), 34.75 (t), 33.92 (t), 31.18 (t), 26.32 (t), 26.05 (t), 23.67 (q), 18.18 (q), 14.46 (q), and 12.39 (q).

Methyl ester of onnamide A(2)

A mixture of onnamide A(1) (18 mg), iodomethane (1 ml), and potassium carbonate (10 mg) in acetone (1 ml) was heated under reflux for 2 hrs. After filtration and concentration, the reaction mixture was separated by TLC (silica gel, 3:1 choloroform-methanol) to give 6.8 mg (37%) of the methyl ester (2) as a light yellow glass: $^1$H NMR (CD$_3$OD) $\delta$7.19 (1H, dd, J=15.0, 11.3 Hz), 6.57 (1H, dd, J=14.8, 11.0 Hz), 6.28 (1H, dd, J=14.9, 11.4 Hz), 6.23 (1H, dd, J=15.3, 10.8 Hz), 6.05 (1H, d, J=15.0 Hz), 5.98 (1H, dt, J=15.1, 8.5 Hz), 5.79 (1H, d, J=9.3 Hz), 5.19 (1H, d, J=6.9 Hz), 4.79 (1H, d, 6.4 Hz), 4.79 (1H, d, J=1.7 Hz), 4.63 (1H, d, J=1.7 Hz), 4.54 (1H, dd, J=8.9, 5.3 Hz), 4.23 (1H, s), 4.16 (1H, dd, J=9.8, 6.5 Hz), 3.97 (1H, dd, J=9.2, 6.5 Hz), 3.87 (1H, dq, J=2.5, 6.6 Hz), 3.73 (3H, s), 3.64 (1H, m), 3.63 (1H, d, J=9.9 Hz), 3.55 (3H, s), 3.46 (1H, dd, J=8.7, 3.8 Hz), 3.25–3.15 (2H, m), 3.23 (3H, s), 2.40 (1H, br d, J=14.4 Hz), 2.31 (1H, dd, J=14.4, 2.3 Hz), 2.25–2.07 (3H, m), 1.92 (1H, m), 1.75 (1H, m), 1.64 (2H, m), 1.62–1.37 (5H, m), 1.30 (1H, m), 1.17 (3H, d, J=6.5 Hz), 1.00 (3H, s), 0.96 (3H, d, J=6.9 Hz), and 0.85 (3H, s): $^{13}$C NMR (CD$_3$OD) $\delta$174.33 (s), 173.71 (s), 168.99 (s), 158.65 (s), 148.23 (s), 143.15 (d), 142.01 (d), 141.09 (d), 131.40 (d), 129.15 (d), 122.96 (d), 110.04 (t), 101.30 (s), 87.63 (t), 80.62 (d), 78.75 (d), 75.56 (d), 74.90 (d), 74.06 (d), 71.04 (d), 70.85 (d×2), 61.91 (q), 53.16 (d), 52.83 (q), 48.75 (q), 43.03 (d), 42.21 (s), 41.85 (t), 37.27 (t), 34.79 (t), 33.92 (t), 29.92 (t), 26.29 (t), 26.00 (t), 23.62 (q), 18.15 (q), 14.41 (q), and 12.36 (q).

Pyrimidine derivation of onnamide A(3)

A mixture of onnamide A(1) (10 mg), 2,4-pentanedione (0.5 ml) and pyridine (0.5 ml) in a sealed tube was heated at 95° C. for 5 hrs. Evaporation of an excess of the reagents under vacuum gave 11 mg (100%) of the pyrimidine derivative (3) as a light yellow glass: UV (MeOH)$\lambda_{max}$202 ($\gamma$22800), 239 (19100), and 299 nm (41200); $^1$H NMR (CD$_3$OD) $\delta$7.17 (1H, dd, J=14.9, 11.2 Hz), 6.55 (1H, dd, J=14.7, 10.7 Hz), 6.39 (1H, s), 6.26 (1H, dd, J=15.1, 11.5 Hz), 6.22 (1H, dd, J=15.1, 10.6 Hz), 6.04 (1H, d, J=15.1 Hz), 5.96 (1H, dt, J=14.2, 6.9 Hz), 5.80 (1H, d, J=9.3 Hz), 5.20 (1H, d, J=6.8 Hz), 4.79 (1H, br s), 4.78 (1H, d, J=6.6 Hz), 4.63 (1H, br s), 4.49 (1H, dd, J=8.3, 4.3 Hz), 4.22 (1H, s), 4.16 (1H, dd, J=9.9, 6.6 Hz), 3.98 (1H, dd, J=9.3, 6.6 Hz), 3.87 (1H, dq, J=2.6, 6.4 Hz), 3.65 (1H, m), 3.64 (1H, d, J=9.7 Hz), 3.55 (3H, s), 3.46 (1H, dd, J=8.5, 4.5 Hz), 3.41 (2H, t, J=6.6 Hz), 3.23 (3H, s), 2.40 (1H, br d, J=14.3 Hz), 2.32 (1H, br d, J=14.4 Hz), 2.26 (6H, s), 2.25–2.05 (3H, m), 1.94 (1H, m), 1.76 (1H, m), 1.69 (2H, m), 1.60–1.40 (5H, m), 1.28 (1H, m), 1.17 (3H, d, J=6.6 Hz), 1.00 (3H, s), 0.95 (3H, d, J=7.0 Hz), and 0.85 (3H, s); $^{13}$C NMR (CD$_3$OD) $\delta$176.67 (s), 174.18 (s), 168,99 (s×2), 168.59 (s), 162.21 (s), 148.12 (s), 142.41 (d), 141.43 (d), 140.63 (d), 131.39 (d), 129.33 (d), 123.69 (d), 110.20 (d), 110.09 (t), 101.23 (s), 87.57 (t), 80.50 (d), 78.72 (d), 75.50 (d), 74.81 (d), 74.03 (d), 71.02 (d×2), 70.75 (d), 61.93 (q), 54.25 (d), 48.76 (q), 42.92 (d), 42.19 (s), 41.62 (t), 37.22 (t), 36.78 (t), 34.77 (t), 33.87 (t), 30.41 (t), 26.98 (t), 25.99 (t), 23.59 (q), 23.43 (q×2), 18.15 (q), 14.34 (q), and 12.36 (q).

ANTITUMOR ACTIVITIES OF THE COMPOSITION OF THE INVENTION

The following assay method was utilized to illustrate the antitumor effectiveness of the compositions of the invention.

P388 MOUSE LEUKEMIA CELL ASSAY

Maintenance of Cell Line

P388 mouse leukemia cells are grown in Dulbecco MEM medium with 10% horse serum, 4 mM glutamine, and 20μg/ml gentamycin (Biologos, Inc.). Cells are incubated in 10% $CO_2$ and subcultured 2 times per week.

PROCEDURE

1. Add composition to each well of a 24-well plate or tube and allow solvent to evaporate to dryness.
2. Add 2 ml (1.2×10$^5$) cells to each well or tube and mix.
3. Incubate in 10% $CO_2$ at 37° C. for 48 hours.
4. Read plates with an inverted microscope, scoring activity from 1+ to 4+ as follows: ND (not detectable), >90%; 1+, 75–90%; 2+, 50–74%; 3+, 25–49%; 4+, <25% of control growth.

Cell counts are performed on each tube and results are reported as percent of control. IC$_{50}$ is the concentration of composition required to inhibit 50% of cell growth.

The results of the above assay are summarized in Table 1.

ANTIVIRAL ACTIVITIES OF THE COMPOSITION OF THE INVENTION

The following assay method was utilized to demonstrate the in vitro antiviral effectiveness of compositions of the invention as reported in Table 2.

ANTIVIRAL ASSAY FOR MOUSE CORONAVIRUS A-59

A. CELL CULTURE: NCTC clone 1469, a derivative of mouse liver.

B. MAINTENANCE OF CELL CULTURE
1. Trypsinization
 a. Aseptically remove the medium.
 b. Rinse cell sheet with 10 ml of $Ca^{++}$ and $Mg^{++}$ free phosphate buffered saline.
 c. Add 4 ml of trypsin-EDTA mixture to a 150 $cm^2$ flask.
 d. Leave for one minute or less and then shake flask.
 e. Add 10 ml of growth medium and break up cell clumps with pipetting.
 f. Count cells.
2. Subcultures for maintenance of cells for assays
 a. Seed 150 $cm^2$ tissue culture flasks with $10 \times 10^6$ cells in 40 ml growth medium.
 b. Subculture 2 times per week.

C. VIRUS

Mouse hepatitis virus strain MHV-A59 classified as a coronavirus.

D. PREPARATION OF PLATES FOR VIRAL ASSAYS
1. Cell Concentration
 a. Dilute the cells with growth medium between $5 \times 10^5$ and $7.5 \times 10^5$ cells per ml.
 b. Seed 24 well trays with 1.0 ml per well.

E. VIRAL ASSAY
1. Dilute drug or extract for test in the appropriate solvent.
2. Add 20 lambda to a 12 mm by 75 mm glass tube for a 16 mm test well.
3. Allow the solvent to evaporate under the laminar flow hood.

Dilute the MHV-A59 in Dulbecco's phosphate buffered saline with $Ca^{++}$ and $Mg^{++}$ to the appropriate predetermined dilution for the lot number currently in use. The dilution of virus in a titration which gives a 3+ to 4+ CPE in 24 hours is used in this assay.

5. Remove medium from wells of plates containing NCTC 1469 cells seeded 24 hours earlier.
6. Add 200 lambda of diluted virus to each test well. Add PBS to control wells.
7. Incubate cells and virus for 1 hour at 37° C.
8. Pour off supernatant at end of incubation period.
9. To each glass tube add 10 lambda of dimethyl sulfoxide (DMSO).
10. Add 1 ml of maintenance medium to each glass tube.
11. Pour the contents of the glass tube into the corresponding well of the tissue culture plate.
12. Incubate infected cells at 37° C. and read the following day.
13. At twelve hours areas of cell fusion are quite apparent and can be detected both visually and microscopically.
14. At 24 hours the CPE is extensive and on stained plates the difference between activity and none is apparent from visual examination.
15. To stain plates discard medium and to each 16 mm well add 200 lambda of methylene blue stain.
16. Leave the stain on the cell sheet for 30 minutes or more.
17. Pour off the stain and wash plates in tap water until the water is clear.
18. Allow plates to dry.
19. Scoring drug activity
 a. Cytotoxicity scoring
  100% = complete cell destruction
  75% = partial cell destruction
  50% = partial cell destruction
  25% = partial cell destruction
  0% = no cytotoxicity
 b. Antiviral activity is scored from 0 to +++.
  +++ = complete inhibition of cytopathic effects and cell fusion
  ++ = partial inhibition
  + = partial inhibition
  +/- = partial inhibition
  0 = no protection F. MEDIA
1. Growth medium for NCTC 1469 cell line
 Medium NCTC 135 (GIBCO Cat. #320-1350)
 10% horse serum
 2% 200 mM 1-glutamine
 1% nonessential amino acids (NEAA) (100×)
 1% sodium pyruvate (110 mg/liter) (100×)
 gentamicin
  10 mg/ml (use 50 μg/ml) or 0.5 ml/100
  50 mg/ml (use 50 μg/ml) or 0.1 ml/100
2. Maintenance medium for viral assay
 Dulbecco's modified Eagle medium @4500 mg/L glucose
 GIBCO Cat. #320-1965
 5% fetal bovine serum (FBS)
 2% 200 mM 1-glutamine
 1% nonessential amino acids (NEAA) (100×)
 1% sodium pyruvate (110 mg/liter) (100×)
 gentamicin (use 50 μg/ml)
3. Trypsin
 GIBCO Cat. #610-5405 trypsin-EDTA (10×)
 5.0 gm trypsin (1:250) and 2.0 gm EDTA/L Prepare 1X solution in Dulbecco's phosphate buffered saline free of $Ca^{++}$ and $Mg^{++}$. Add 1.1 grams glucose per liter.
4. Stain
 Methylene Blue-certified
 Sigma No. M 9140
 50% ethanol:water
 5 grams methylene blue/liter

Antiviral Disc Assay fr VSV and HSV-1

A. Maintenance of Cell Cultures
1. Virus
 a. Both herpes simplex type 1 (HSV-1) and vesicular stomatitis virus (VSV) replicate in the CV-1 cell line. CV-1 is a fibroblast-like cell culture derived from primary African green monkey cells.
2. Growth of CV-1 Cells
 a. Seed 150 $cm^2$ tissue culture flasks each with $10 \times 10^6$ CV-1 cells in 40 ml of EMEM with 10% PBS (growth medium).
 b. Seven days after seeding the flasks cell numbers should be approximately $40-50 \times 10^6$ cells. CV-1 cells have a doubling time of 72 hours based on these numbers.

3. Trypsinization
 a. Aseptically remove the medium.
 b. Rinse cell sheet with 10 ml of Ca++ and Mg++ free Dulbecco's phosphate buffered saline or Pucks G saline at least twice.
 c. Add 4.0 ml of trypsin −EDTA mixture.
 d. Incubate flask at room temperature with occasional rocking until the cells detach from the flask (about 5 min).
 e. Shake flask.
 f. Add 10 ml EMEM growth medium and break up cell clumps with pipetting.
 g. Count cells.

B. Preparation of plates for viral assays
 1. Cell Concentration
  a. Dilute the cells with EMEM to $4 \times 10^5$ cells/ml.
  b. Seed 24 well trays with 0.5 ml per well. Cell concentration per well is $2 \times 10^5$ cells.
  c. Incubate at 37° C. with 5% $CO_2$.
  d. The wells can be uses over the next several days beginning the day after seeding (preferably 2, 3, or 4).

C. Assay of HSV-1 and VSV in CV-1 cells
 1. Infection of CV-1 cells in plates with virus
  a. Remove medium from wells.
  b. Infect well with at least 25 and no more than 80 plaque forming units (PFU) of virus.
  c. Incubate infected cells at 37° C. for 1.0 hour.
  d. Pour off supernatant at end of incubation period.
  e. Add 0.5 ml of methylcellulose overlay medium (MCO which is a maintenance medium without phenol red made with 1% 4000 centipose methylcellulose. FBS is used at 5% level). 2. Drug Evaluation
  a. For drug evaluation wet filter paper discs (6 mm diameter) with approximately 0.02 ml of marine extract or test compound.
   (1) Allow solvent to evaporate for 20 to 30 minutes at room temperature.
   (2) Place discs in the well containing CV-1 cells, virus, and MCO.
  b. Incubate tissue culture plates for 48 hours at 37° C.
  c. After 48 hours place 0.5 ml NRMCO on each well. NRMCO is a maintenance overlay medium without phenol red containing 0.1 mg neutral red dye per ml and 2% 15 centipoise methylcellulose.
  d. Incubate plates at 37° C. and read the following day. Antiviral activity should be observed from two parameters. One is actual reduction in the number of plaques and two is the diminution in plaque diameter.
 3. Scoring Drug Activity
  a. Antiviral activity is scored from 0 to +++.
   +++ =complete inhibition of plaque formation
   ++ =partial inhibition
   + =partial inhibition
   +/− =partial inhibition
   0 =no protection
  b. Cytotoxicity
Wells of 24 well tissue culture plates are 16 mm in diameter. Discs are 6 mm in diameter. Zones of cytotoxicity greater than 6 mm are graded from 8 to 16 using only even numbers.
   0 =no visual or microscopic cytotoxicity
   16 =Complete cell destruction
   8, 10, 12, 14 =partial cytotoxicity

ANTIFUNGAL ACTIVITIES OF THE COMPOSITIONS OF THE INVENTION

The following assay method was utilized to demonstrate the in vitro antifungal effectiveness of compositions of the invention as reported in table 3.

Preparation of inoculum

*Candida albicans:* *C. albicans*(Ca) is grown on Sabouraud dextrose agar to produce single colonies one of which is used to inoculate Sabouraud dextrose broth. The broth is incubated at 37° C. with shaking at 200rpm for 18hrs., the resultant culture is frozen with 10% (v/v) glycerol at −80° C. and used as the inoculum for the anti-Candida assay.

Assay protocols

1. Disc diffusion assay

*C. albicans* is inoculated into melted Sabouraud dextrose agar at 45° C. to give a cell density of approximately 1000 cells/mL. Plates are prepared with 10mL of the seeded agar in a 10cm ×10cm petri dish. These plates are stored at 4° C. until needed for the assay.

Paper discs (6.35mm) are impregnated with the test substance and allowed to dry. They are then placed onto the surface of a test plate prepared as detailed above. Plates are incubated overnight at 37° C. after which time the zones of growth inhibition can be read, these are expressed as the diameter of the zone in millimeters.

2. Minimum inhibitory concentration (MIC)

Two-fold dilutions for the drug are prepared in 50μL volumes of Sabouraud dextrose broth using 96-well microtiter plates. An inoculum of *C. alibicans* is added in a small volume to give a cell density of approximately 1000 cells/mL. Plates are incubated at 37° C. overnight. 10uL of Triphenyl tetrazolium chloride (1% w/v) is then added to each well; a further 2 hour incubation results in a deep coloration of the microorganism. The MIC is the lowest concentration of the drug which has completely inhibited growth.

TABLE 1

| Antitumor Activity Against Mouse P388: | |
|---|---|
| Composition | $IC_{50}$ (μg/ml) |
| Onnamide A (1) | 0.001 |
| Methyl ester (2) | 0.3 |
| Pyrimidine (3) derivative | 0.003 |

TABLE 2

| | | Antiviral Activity | | | | | |
|---|---|---|---|---|---|---|---|
| | Dose | HSV-1 | | VSV | | A-59 | |
| Composition | (ug/well) | CYT | AV | CYT | AV | CYT | AV |
| Onnamide A (1) | 20 | 0 LS | 3+ | 0 LS | 3+ | 25 | 3+ |
| | 2 | 0 LS | 3+ | 0 LS | 3+ | 25 | 3+ |
| | 0.2 | 0 LS | 3+ | 0 LS | 3+ | 25 | 3+ |
| | 0.02 | 0 | 2+ | 0 LS | 2+ | 25 | 3+ |
| | 0.004 | 0 | +/− | 0 | 2+ | 0 | 3+ |
| | 0.002 | 0 | — | 0 | — | 0 | 2+ |
| | 0.0002 | | | | | 0 | — |
| Methyl ester (2) | 20 | 0 LS | 3+ | 0 LS | 3+ | 25 | 3+ |
| | 2 | 0 LS | 3+ | 0 LS | 3+ | 25 | 3+ |
| | 0.2 | 0 LS | 3+ | 0 LS | 3+ | 25 | 3+ |
| | 0.02 | 0 | 2+ | 0 LS | 2+ | 25 | 3+ |
| | 0.004 | 0 | 2+ | 0 | 1+ | 0 | 3+ |
| | 0.002 | 0 | 2+ | 0 | 1+ | 0 | 3+ |
| | 0.0002 | 0 | — | | | 0 | 3+ |
| | 0.0001 | | | | | 0 | — |
| Pyrimidine | 20 | 0 LS | 3+ | 0 LS | 3+ | 25 | 3+ |

TABLE 2-continued

| Composition | Dose (ug/well) | Antiviral Activity | | | | | |
|---|---|---|---|---|---|---|---|
| | | HSV-1 | | VSV | | A-59 | |
| | | CYT | AV | CYT | AV | CYT | AV |
| derivative (3) | 2 | 0 LS | 3+ | 0 LS | 3+ | 25 | 3+ |
| | 0.2 | 0 LS | 3+ | 0 LS | 3+ | 25 | 3+ |
| | 0.02 | 0 | 2+ | 0 | 2+ | 25 | 3+ |
| | 0.004 | 0 | 2+ | 0 | — | 0 | 3+ |
| | 0.002 | 0 | — | 0 | — | 0 | 3+ |
| | 0.0002 | | | | | 0 | 3+ |
| | 0.0001 | | | | | 0 | — |

TABLE 3

| Antifungal Activity against *Candida albicans*: | |
|---|---|
| Composition | MIC (μg/ml) |
| Onnamide A (1) | 50 |
| Methyl ester (2) | 5 |
| Pyrimidine (3) derivative | 50 |

The above data reports the in vitro activity determined for compositions of the invention for inhibiting various tumor cells, viruses and fungi. The above results indicate, as would be known to those skilled in the art, that the compositions of the invention are useful for inhibiting tumors, viruses and fungi in hosts and the diseases caused thereby.

The scope of the present invention is not limited by the description, examples, and suggested uses herein and modifications can be made without departing from the spirit of the invention. The compositions described herein may have other useful applications such as, for example, analgesic applications. Therapeutic application of the compositions of the present invention can be accomplished by any suitable therapeutic method and technique as is presently or prospectively known to those skilled in the art. Further, the composition of the invention may have use as a starting material or intermediate for the preparation of other useful compositions. Thus, it is intended that the present invention cover the modifications and variations of this invention provided that they come within the scope of the appended claims and their equivalents.

What is claimed is:

1. A compound according to the formula:

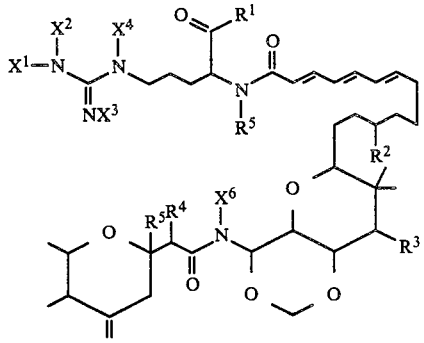

wherein $X^1$-$X^4$ are the same or different and are hydrogen, hydroxyl, lower alkanoyl, or lower alkyl; $X^5$-$X^6$ are the same or different and are hydrogen or lower alkyl; $R^1$ is a hydrogen, hydroxyl, lower alkyl or lower alkoxy; $R^2$-$R^5$ are the same or different and are hydrogen, hydroxyl, lower alkoxy or lower alkanoyloxy and the analogs thereof wherein the double bonds are partially or fully reduced.

2. A compound of claim 1 of the formula:

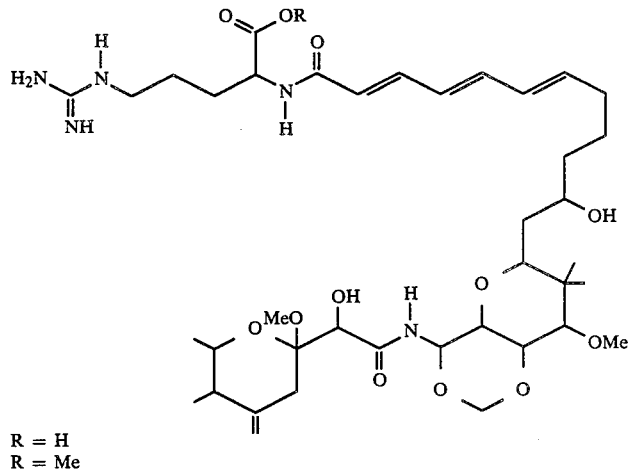

R = H
R = Me

3. A compound of claim 1 which is substantially pure.

4. A pharmaceutical composition comprising, as an active ingredient, an effective antiviral amount of a compound of claim 1 and a non-toxic pharmaceutically acceptable carrier of diluent.

5. A pharmaceutical composition comprising, as an active ingredient, an effective antiviral amount of a compound of claim 2 and a non-toxic pharmaceutically acceptable carrier of diluent.

* * * * *